Figure 1:
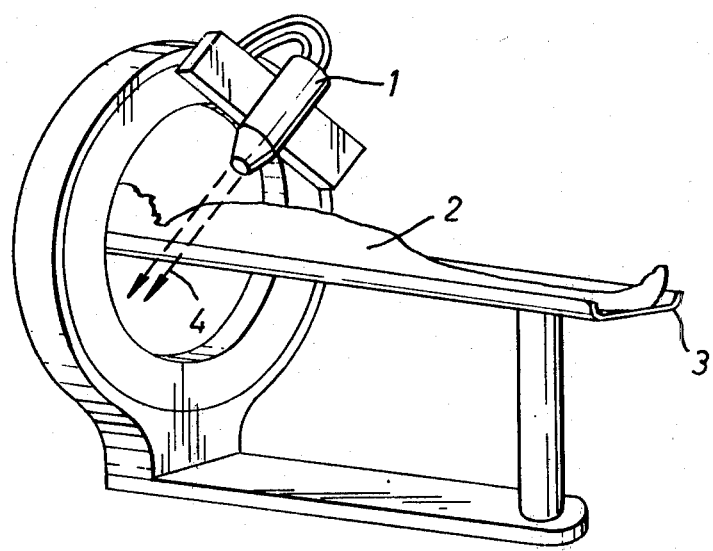

United States Patent [19]

Froggatt

[11] 4,118,631
[45] Oct. 3, 1978

[54] RADIOGRAPHIC APPARATUS
[75] Inventor: Robert Justin Froggatt, Southall, England
[73] Assignee: EMI Limited, Hayes, England
[21] Appl. No.: 781,409
[22] Filed: Mar. 25, 1977
[30] Foreign Application Priority Data
Mar. 30, 1976 [GB] United Kingdom .............. 12679/76
[51] Int. Cl.$^2$ .......................... A61B 6/00; A61N 5/00
[52] U.S. Cl. ........................ 250/492 R; 250/416 TV; 250/445 T
[58] Field of Search ........ 250/445 T, 416 TV, 492 R, 250/491, 369

[56] References Cited
U.S. PATENT DOCUMENTS
3,777,124  12/1973  Pavkovich ........................... 250/454
FOREIGN PATENT DOCUMENTS
1,152,442  5/1969  United Kingdom ..................... 250/491

Primary Examiner—Alfred E. Smith
Assistant Examiner—T. N. Grigsby
Attorney, Agent, or Firm—Cooper, Dunham, Clark, Griffin & Moran

[57] ABSTRACT

In therapeutic radiographic apparatus it is desirable to maintain the penetrating radiation in passing through tissue to be irradiated, rather than surrounding healthy tissue, despite movements of the patient. A shadowgraph radiographic picture of part of the patient is obtained by derivation from cross-sectional radiographic pictures from computerized axial tomography (CAT) apparatus. A similar shadowgraph picture is obtained, during therapy treatment, by collecting the therapy radiation after passing through the body. The two pictures are compared to determine the position of the therapy radiation relative to the tissue to be irradiated and the position is adjusted in response to the comparison.

11 Claims, 4 Drawing Figures

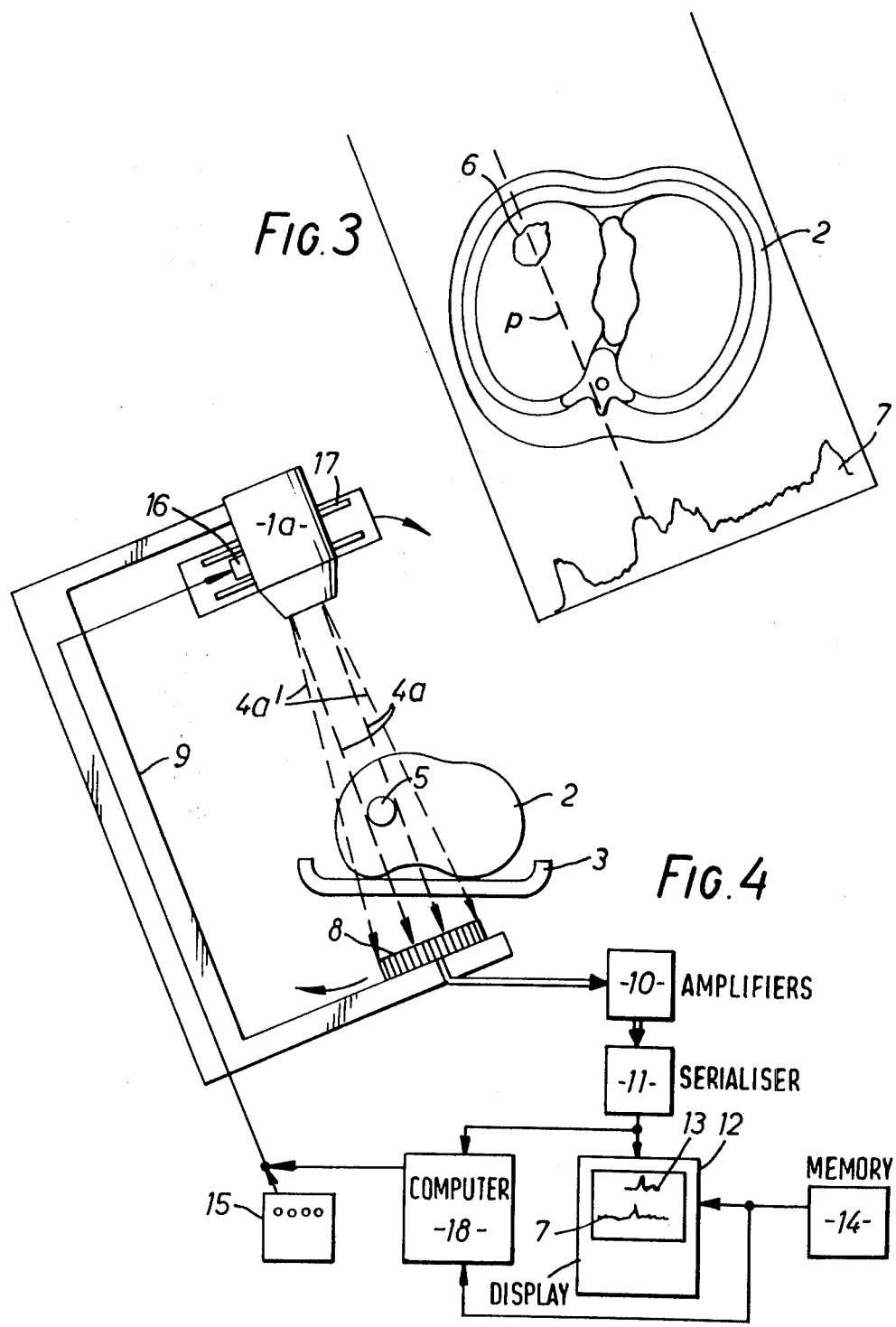

RADIOGRAPHIC APPARATUS

The present invention relates to radiographic apparatus for therapeutic purposes. Known radiation therapy apparatus for the treatment of tumours comprises sources of high energy penetrating radiation, for example X- or γ-radiation, which is directed selectively at a region, of a patient, including a tumour. The radiation is in the form of one or more beams suitably shaped so that a maximum of radiation passes through the tumour and a minimum through surrounding tissue. It is also usual to employ a plurality of different sources of such beams or to move single source about the patient's body to provide a plurality of beams. Thus, if care is taken that all such beams pass through the tumour, it is possible to subject the tumour to considerably more radiation than surrounding healthy tissue.

It is, of course, important that the beams of radiation pass through the tumour throughout a relatively lengthy treatment. For this purpose it is desirable to restrict motion of the patient. However, for very precise irradiation of small tumours with narrow beams of radiation, body motions such as those due to breathing, heart motion, peristalsis and similar may become important so that accurate methods of keeping the radiation beams aligned are required.

It is an object of this invention to provide an arrangement for placing and maintaining such beams in a desired position in relation to a chosen part of a body.

According to one aspect of the invention there is provided a therapeutic radiographic apparatus including a source of penetrating radiation, means for directing the radiation along a path through a predetermined region of the body of a patient, means disposed to receive radiation after passage through the said body to provide a representation of the part of the body traversed by the radiation, means for comparing the said representation with a previously derived representation on which a feature of interest has been identified, and adjustment means for changing the path of the radiation to correlate the features of interest in the two representations.

According to a further aspect of the invention there is provided a method of directing a beam of penetrating radiation, provided by a therapeutic radiographic apparatus, along a path through a predetermined region of the body of a patient under examination including the steps of:

(a) deriving a representation of a part of the said body including at least one feature having a known relationship to the said region;

(b) detecting the said radiation after passage through the body to derive a further representation including the said feature;

(c) comparing the said representations so that differences between the positions of the at least one feature in the two representations indicate the position of the said radiation in relation to the said region; and (d) changing the path of the radiation to reduce the said differences and thereby direct the radiation more closely to the said region.

Figure 2:
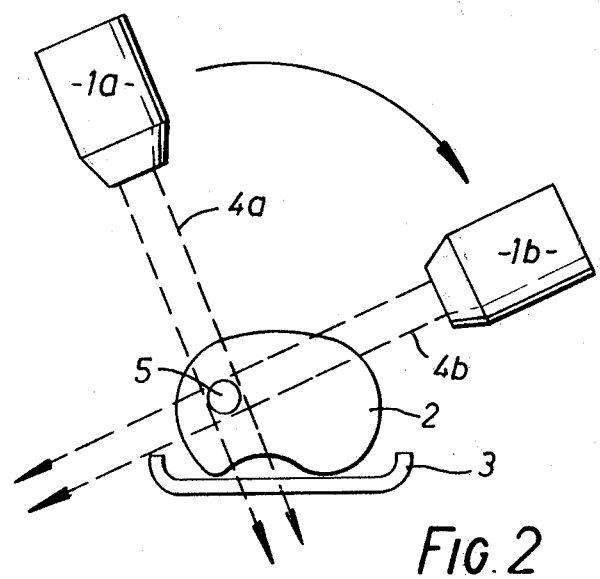

In order that the invention may be clearly understood and readily carried into effect an example thereof will now be described with reference to the accompanying drawings of which, FIG. 1 shows in simplified form one example of a therapeutic radiographic apparatus, FIG. 2 is indicative of the manner in which penetrating radiation irradiates a chosen part of the body of a patient, FIG. 3 indicates the nature of a shadowgraph X-ray picture of a part of the body and FIG. 4 illustrates the method of the invention of maintaining the radiation in passage through that part.

There is shown in FIG. 1 a simplified drawing of a conventional X-ray therapy apparatus including an X-ray source 1 which is arranged to move about the body 2 of a patient lying on a bed 3 so that a beam 4 of X-rays is directed at all times in the motion through a predetermined region of the patient so as to include a tumour to be irradiated. For the purposes of the following explanation it will be assumed that the motion is such that the beam of radiation lies at all times in a single plane and rotates in that plane about an axis perpendicular thereto, preferably passing through the tumour. This motion is illustrated in FIG. 2 in which many conventional features are not specifically indicated since the machine may be of any one of a number of well known types of γ- or X-ray therapy machines. The source 1 is arranged to move at least between positions 1a and 1b so that the beam 4 moves from 4a to 4b. It can be seen that in the absence of body motion the limited region 5 including a tumour is irradiated continuously but that other regions of the body receive less radiation. The use of narrower beams of radiation than those shown in FIG. 2 allows the irradiation of smaller regions such as 5. However it is necessary to determine the position of the region including a tumour with greater accuracy in such cases and it is also necessary to prevent movements of the patient from shifting the tumour from the highly irradiated region.

One means of accurately determining the position of a tumour in a cross-section of a patient, such as that shown in FIG. 2 is provided by recent developments in an X-ray examination technique known as Computerised Axial Tomography (CAT). CAT equipment, such as that described in the specification of U.S. Pat. No. 3,778,614 provides an accurate representation of the distribution of X-ray absorption, in such a cross-section, from which the locations of tumours may be determined.

FIG. 3 shows a simplified CAT cross-sectional picture of a patients body with a spot representing a tumour in a lung at 6. It will be understood that such a cross-sectional picture is normally provided as a television display of a matrix of elements each having an intensity proportional to an absorption value. However since a data store cooperating with the display holds the absorption values for each matrix element it is possible to derive further data from those values.

In the present invention the data is used to provide for each of a number of views at different directions through the equivalent to a strip form of "shadowgraph", or normal X-ray picture, as if provided on an X-ray film by X-rays travelling in that direction. This is achieved by forming in the cross-section plane a number of notional lines, such as $p$, parallel to each direction and summing the X-ray absorption for all elements of the cross-sectional picture on each line. This may readily be achieved by a simple computer program, withdrawing data from store for the appropriate address, but could also be carried out by hand using a print-out of the CAT data. A typical shadowgraph strip is shown at 7 in FIG. 3 and it will be seen that in addition to peaks for strongly absorbing features such as a bone there is a well defined peak for the tumour 6. It should be noted that the shadowgraph strip shown is purely illustrative and should not be taken to be an accurate representation of an actual strip.

Using such a shadowgraph strip for each of several angular positions of the X-source 1 the position of the source is adjusted in a direction in the plane perpendicular to the X-rays to keep the beam 4 passing through region 5. For this purpose X-ray detection means 8 are provided as shown in FIG. 4 on the opposite side of the body 2 to the source but linked to it by a rigid yoke 9 to share in its motion. The source is arranged to provide not only the narrow therapy beam 4 but a wider beam 4' of lower intensity but of sufficient extent to irradiate substantially all of detector means 8. This may be a penumbra of the source collimation, scattering within the body near the point of entry of beam 4, or may even be provided by an auxiliary source operated with or in alternation with the main source. A similar effect may be achieved by defocussing the electron beam on the X-ray anode.

In this example detector means 8 comprises a strip of individual detectors sensitive to X-rays, for example scintillation crystals and associated photomultipliers. Alternatively a fluoroscopic screen could be used.

The outputs of the detectors are amplified in amplifiers 10 and serialised in circuits 11 for display at a television type display 12 to provide a shadowgraph strip 13, similar to strip 7 but for a limited region illuminated by beam 4'. It will be appreciated that the intensity of the central beam 4 will be much greater than that of peripheral beam 4'. The detectors or following circuits should be appropriately adjusted to account for the difference. This can be achieved by preadjustment in the absence of a body 2. Alternatively an appropriate attenuator can be inserted in the radiation path.

The strips 7 are stored in memory circuit 14 and an appropriate one can be provided for display on 12 for comparison purposes. A control panel 15 is also provided, at which an operator can control a motor 16 driving source 1 in tracks along its mounting as the rotational frame, not shown.

In the course of rotation of source 1 and detectors 8 the shadowgraph 7 is updated. This should be a continuous change throughout the rotation but in practice a limited number of different shadowgraphs 7 will suffice.

It should be noted that, since the expected body movements are relatively small, the X-ray beam 4 can be restricted by movable collimators rather than by movement of the relatively bulky source 1. In that case independent motion of detectors 8 should be provided. The movement should be appropriately related to the movement of beam 4.

It will be appreciated that, of shadowgraphs 7 taken from different dispositions, not all will clearly show a tumour. All should, however, show features in that region. It is therefore desirable in patient preparation to determine a marker part of each shadowgraph 7 which aligns with tumour 6 in the respective direction and which should, therefore, be centred in beam 4. Automatic means may be used for this purpose but preferably it should be carried out carefully by a radiographer. For a limited number of shadowgraphs 7 this would require no more time than conventional therapeutic patient preparation.

In operation, the patient is first aligned, in an initial position probably with beam 4 to be vertical, so that the tumour lies approximately at the centre of rotation. This can be achieved by motion of the patient on bed 3 but preferably motorised motion of bed 3 is provided. The first example of shadowgraph 7 is also lined up on the screen of display 12 so that the marker of that shadowgraph is placed at a vertical position, normally the centre, corresponding to the output of the centre of array 8 as seen at 13.

It can be seen that, when beams 4 and 4' are initiated, the shorter shadowgraph 13 is displayed and includes representation of the marker feature, provided initial alignment of the rotational axis was adequate. The source 1 and detectors 8 can then be traversed to correlate these features of the two shadowgraph strips. In the course of further examination the body may move; which will thus move the marker feature of shadowgraph 13. Recorrelation of the two features by movement of source 1 can then realign the beam 4 with tumour 6 in region 5.

As rotation proceeds the shadowgraph 7 is updated, as mentioned hereinbefore, and each marker region, which was predetermined, is set up at the appropriate position on the screen of display 12.

Since the therapeutic apparatus operates at a relatively slow rate it is possible for an operator to control source 1 to keep the two features aligned. However a suitably programmed digital computer 18 can also be provided. This can receive both the detector output and shadowgraphs 18 from store 14 and correlate them to provide an error signal for automatic control of source 1. The correlation can be readily achieved by many techniques known for pattern recognition devices or automatic radar tracking. To facilitate the computerised alignment of shadowgraphs 7 they can be provided with suitable alignment pulses well separated from the region of interest.

It will be realised that the invention is not limited to two-dimensional motion in a single plane. A plurality of CAT pictures such as that shown in FIG. 3 can be used to derive, in the manner described, a two dimensional, rather than strip, shadowgraph, essentially like a normal X-ray picture. This can be compared with a similar shadowgraph from a detector means 8 extended to a two dimensional array. The comparison on display 12 would then be by complete overlay of the two pictures while the known comparison techniques for computer 18 are readily capable of two dimensional correlation. Two dimensional movement of source 1 or the alternative X-ray collimators should then be provided. Tumours can be readily detected in CAT diagnosis and, together with surrounding features should be sufficiently distinct for application of the invention. However if they are not sufficiently clear other surrounding features of the body whose positions are known in relation to the tumours, such as bones or even features introduced for the purpose, can be used as alternatives.

It should be understood that, although the apparatus shown herein is representative of one kind of therapeutic X-ray apparatus, the invention may be used in conjunction with many different examples of such apparatus.

What I claim is:

1. A therapeutic radiographic apparatus including a source of pentrating radiation, means for directing the radiation along a path through a predetermined region of the body of a patient, means disposed to receive radiation after passage through said body to provide a representation of the part of the body traversed by the radiation, means for comparing the said representation with a previously derived representation on which a feature of interest has been identified, and adjustment means for changing the path of the radiation to correlate the features of interest in the two representations.

2. An apparatus according to claim 1 in which the adjustment means comprises means for moving the source and the detector means in a direction perpendicular to the said path.

3. An apparatus according to claim 1 in whch the means for comparing includes a display arranged to display the two representations so that the feature of interest of the previously derived representation is aligned with that part of the other representation relating to the centre of the detector means and including means for directing the adjustment means until the features of interest are correlated.

4. An apparatus according to claim 1 including a computer arranged to compare the two representations and to direct the adjustment means to correlate the features of interest.

5. An apparatus according to claim 1 in which each representation is a shadowgraph strip of a section of the body as viewed from one direction.

6. An apparatus according to claim 1 in which the detector means is a plurality of detector devices.

7. A method of directing a beam of penetrating radiation, provided by a therapeutic radiographic apparatus, along a path through a predetermined region of the body of a patient under examination including the steps of:
 (a) deriving a representation of a part of the said body including at least one feature having a known relationship to the said region;
 (b) detecting the said radiation after passage through the body to derive a further representation including the said feature;
 (c) comparing the said representations so that differences between the positions of the at least one feature in the two representations indicate the position of the said radiation in relation to the said region; and
 (d) changing the path of the radiation to reduce the said differences and thereby direct the radiation more closely to the said region.

8. A method according to claim 7 in which the representations derived are shadowgraph representations.

9. A method according to claim 8 in which the first mentioned shadowgraph representation is derived from a crossectional representation of the body.

10. A method according to claim 8 in which the representations are strip shadowgraphs of a section viewed from one direction.

11. A method according to claim 7 including the step of repeating steps (b) to (d) for different angular positions of the beam in the body using different ones of the first representation obtained by repetition of step (a) for the respective position.

* * * * *